United States Patent [19]
Urch et al.

[11] Patent Number: 5,849,754
[45] Date of Patent: Dec. 15, 1998

[54] BICYCLIC AMINE DERIVATIVES

[75] Inventors: Christopher John Urch; Terence Lewis; Raymond Leo Sunley, all of Bracknell, United Kingdom

[73] Assignee: Zeneca Limited, London, England

[21] Appl. No.: 969,634

[22] Filed: Nov. 13, 1997

[30] Foreign Application Priority Data

Nov. 20, 1996 [GB] United Kingdom .................... 9624114

[51] Int. Cl.[6] ........................ A61K 31/46; C07D 411/04; C07D 401/04; C07D 409/04
[52] U.S. Cl. ............................................ 514/304; 546/126
[58] Field of Search .............................. 546/126; 514/304

[56] References Cited

U.S. PATENT DOCUMENTS

| | | | |
|---|---|---|---|
| 3,120,537 | 2/1964 | Archer et al. ........................... | 260/291 |
| 3,133,073 | 5/1964 | Archer ..................................... | 260/292 |
| 3,308,131 | 3/1967 | McKusick ............................... | 260/294 |
| 3,501,461 | 3/1970 | Newallis et al. ........................ | 260/239 |
| 3,546,232 | 12/1970 | Kaiser et al. ........................... | 260/292 |
| 3,556,943 | 1/1971 | Fonken et al. ......................... | 195/51 |
| 3,657,257 | 4/1972 | Helsley et al. ......................... | 260/292 |
| 4,180,669 | 12/1979 | Winn ...................................... | 546/240 |
| 4,393,069 | 7/1983 | Langbein et al. ...................... | 424/265 |
| 4,590,270 | 5/1986 | Kompis et al. ......................... | 544/320 |
| 4,774,249 | 9/1988 | Kompis et al. ......................... | 514/272 |
| 5,491,148 | 2/1996 | Berger et al. .......................... | 514/305 |

FOREIGN PATENT DOCUMENTS

| | | |
|---|---|---|
| 0 031 219 | 7/1981 | European Pat. Off. . |
| 0 216 625 | 4/1987 | European Pat. Off. . |
| 0 307 142 | 3/1989 | European Pat. Off. . |
| 0 315 390 | 5/1989 | European Pat. Off. . |
| 0 398 578 | 11/1990 | European Pat. Off. . |
| 0 498 331 | 8/1992 | European Pat. Off. . |
| 0 518 805 | 12/1992 | European Pat. Off. . |
| 2 548 666 | 1/1985 | France . |
| 27 49 584 | 5/1978 | Germany . |
| 1 061 472 | 3/1967 | United Kingdom . |
| 1 304 649 | 1/1973 | United Kingdom . |
| 91/17156 | 11/1991 | WIPO . |
| 92/01688 | 2/1992 | WIPO . |
| 93/00313 | 1/1993 | WIPO . |
| 93/14636 | 8/1993 | WIPO . |
| 93/25527 | 12/1993 | WIPO . |
| 95/03306 | 2/1995 | WIPO . |
| 96/08968 | 3/1996 | WIPO . |
| 96/37494 | 11/1996 | WIPO . |
| 9637494 | 11/1996 | WIPO . |
| 97/13770 | 4/1997 | WIPO . |
| 97/43286 | 11/1997 | WIPO . |

OTHER PUBLICATIONS

Archer, S., et al., J. Am. Chem. Soc., "The Action of Nucleophilic Agents on 3 α–Chlorotropane," vol. 80, 1958, pp. 4677–4681.

Bell, M.R., et al., J. Am. Chem. Soc., "Ethyl 3α–Phenyltropane–3β–carboxylate and Related Compounds," vol. 82, No. 7–9, 1960, pp. 4638–4641.

Cignarella, G., et al., J. Am. Chem. Soc., "A New Synthesis of Tropane Derivatives," vol. 83, No. 10–12, 1961, pp. 4999–5003.

Daum, S. J., et al., J. Med. Chem., "Analgesic Activity of the Epimeric Tropane Analogs of Meperidine. A Physical and Pharmacological Study," vol. 18, No. 5, 1975, pp. 496–501.

Gutkowska, B., et al., Acta Polon. Pharm., "Syntezy Niektorych Pochodnych 8–Alkilo–8–Aza–Bicyklo[3.2.1] Oktan–3–Onu," vol. 38, No. 4, 1981, pp. 411–415.

Lowe, J. A., et al., J. Med. Chem., "Aza–Tricyclic Substance P Antagonists," vol. 37, No. 18, 1994, p. 2831.

(List continued on next page.)

Primary Examiner—Bernard Dentz
Attorney, Agent, or Firm—Marian T. Thomson

[57] ABSTRACT

The present invention concerns bicyclic amine derivatives of formula (I):

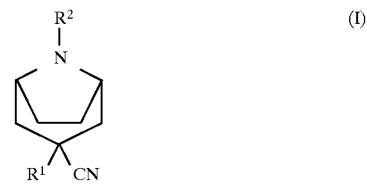

wherein $R^1$ is an optionally substituted 5-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to eight carbon atoms, and wherein two substituents may join to form a fused ring; $R^2$ represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or $XR^3$ (where X represents oxygen or a group $NR^4$), provided that when $R^2$ is alkenyl, aralkenyl or alkynyl said group does not have an unsaturated carbon atom bonding directly to the ring nitrogen of formula (I); $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of $R^2$, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; or an acid addition salt, quaternary ammonium salt or N-oxide derived therefrom; to processes for preparing them, to insecticidal compositions comprising them and to methods of using them to combat and control insect pests.

11 Claims, No Drawings

OTHER PUBLICATIONS

Maag, H., et al., Helvetica Chimica Acta, "94.5–(N–Arylnortropan–3–yl)–and 5–(N–Arylpiperidin–4–yl)–2,4–diaminopyrimidines. Novel Inhibitors of Dihydrofolate Reductase," vol. 69, No. 4, 1986, pp. 887–897.

Repke, D. B., et al., J. Org. Chem., "Abbreviated Ibogaine Congeners. Synthesis and Reactions of Tropan–3–yl–2–and –3–indoles. Investigation of an Unusual Isomerization of 2–Substituted Indoles Using Computational and Spectroscopic Techniques," vol. 59, No. 8, 1994, pp. 2164–2171.

Zirkle, C. L., et al., J. Org. Chem., "Isomeric 3–Oxa–and 3–Thiagranatanin–7–ols and Their Derivatives; Reduction of Bicyclic Amino Ketones Related to Tropinone," vol. 26, 1961, pp. 395–407.

BICYCLIC AMINE DERIVATIVES

This invention relates to novel bicyclic amines, to processes for preparing them, to insecticidal compositions comprising them and to methods of using them to combat and control insect pests.

The invention provides a compound of formula (I):

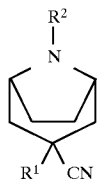

wherein $R^1$ is an optionally substituted 5-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to eight carbon atoms, and wherein two substituents may join to form a fused ring; $R^2$ represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or $XR^3$ (where X represents oxygen or a group $NR^4$), provided that when $R^2$ is alkenyl, aralkenyl or alkynyl said group does not have an unsaturated carbon atom bonding directly to the ring nitrogen of formula (I); $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of $R^2$, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, amino, acylamino, imidate and phosphonato groups; aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl, dithiocarboxyl moieties of $R^2$, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; or an acid addition salt, quaternary ammonium salt or N-oxide derived therefrom.

It will be appreciated that the bicyclic amine compounds of formula (I) are capable of existing in more than one isomeric form since the groups R' and CN may be positioned in either an exo or endo relationship, and the present invention embraces within its scope both exo and endo forms and mixtures thereof in all proportions and also any further isomeric variants arising from cis and trans substitution patterns or chiral centres present in either of $R^1$ or $R^2$.

Examples of 5-membered ring systems represented by $R^1$ include those based on pyrrole, pyrazole, imidazole, 1,2,3- and 1,2,4-triazoles, furan, thiophene, oxazole, isoxazole, thiazole, isothiazole, 1,2,3- and 1,3,4-oxadiazoles, and 1,2,3- and 1,3,4-thiadiazoles, and partially reduced forms of these containing one double bond, as well as those based on oxathiole, dioxole, and dithiole rings containing one double bond.

When two substituents on $R^1$ join to form a ring the resulting ring system is, for example, indole, benzofuran, benzoxazole, benzothiophen or benzimidazole.

Halogen includes fluorine, chlorine, bromine and iodine.

Alkyl moieties preferably contain from 1 to 6, more preferably from 1 to 4, carbon atoms. They can be in the form of straight or branched chains, for example methyl, ethyl, n- or iso-propyl, or n-, sec-, iso- or tert-butyl.

Haloalkyl is preferably $C_{1-6}$ haloalkyl, especially fluoroalkyl (for example trifluoromethyl, 2,2,2-trifluoroethyl or 2,2-difluoroethyl) or chloroalkyl. For $R^2$, haloalkyl is preferably $C_{2-6}$ haloalkyl wherein there is no halogen on the α-carbon (for example 2,2,2-trifluoroethyl or 2,2-difluoroethyl).

Alkenyl and alkynyl moieties as substituents of R' preferably contain from 2 to 6, more preferably from 2 to 4, carbon atoms. They can be in the form of straight or branched chains, and, where appropriate, the alkenyl moieties can be of either (E)- or (Z)- configuration. Examples are vinyl, allyl and propargyl.

Aryl includes naphthyl but is preferably phenyl.

Heteroaryl includes 5- and 6-membered aromatic rings containing one, two, three or four heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl (1,2,3-, 1,2,4- and 1,3,5-), furyl, thienyl, pyrrolyl, pyrazolyl, imidazolyl, triazolyl (1,2,3- and 1,2,4-), tetrazolyl, oxazolyl, isoxazolyl, thiazolyl, isothiazolyl, oxadiazolyl, thiadiazolyl, quinolinyl, isoquinolinyl, cinnolinyl, quinazolinyl, quinoxalinyl, indolinyl, isoindolinyl, benzofuranyl, benzothienyl and benzimidazolinyl.

The heterocyclyl moiety of heterocyclylalkyl is a ring containing one or two heteroatoms selected from the list comprising oxygen, sulphur and nitrogen. Examples are piperidine, piperazine, pyrrolidine, tetrahydrofuran, morpholine, thietane, pyridine or thiazole.

The alkylenedioxy group is a substituent for a ring and is especially $C_{1-4}$ alkylenedioxy. Alkylenedioxy groups are optionally substituted with halogen (especially flourine) and are, for example, methylenedioxy ($OCH_2O$) or difluoromethylenedioxy ($OCF_2O$).

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

In one particular aspect the present invention provides a compound of formula (I), wherein $R^1$ is an optionally substituted 5-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl (especially $C_{1-4}$ alkyl), alkenyl (especially $C_{2-4}$ alkenyl), alkynyl (especially $C_{2-4}$ alkynyl), alkoxy (especially $C_{1-4}$ alkoxy), haloalkyl (especially $C_{1-4}$ haloalkyl), haloalkenyl (especially $C_{2-4}$ haloalkenyl), alkylthio (especially $C_{1-4}$ alkylthio), and alkyl amino (especially mono- or di- ($C_{1-4}$ alkyl)amino, such as mono- or di- ($C_{1-3}$ alkyl)amino) groups, any of which groups contain up to eight carbon atoms, and wherein two substituents may join to form a fused ring; $R^2$ represents hydrogen or cyano or a group selected from alkyl (especially $C_{1-4}$ alkyl), aryl (especially phenyl), heteroaryl (especially pyridinyl or pyrimidinyl), aralkyl (especially aryl($C_{1-4}$)alkyl, such as phenyl($C_{1-4}$) alkyl), heteroarylalkyl (especially heteroaryl ($C_{1-4}$)alkyl, such as pyridinyl($C_{1-4}$)alkyl or pyrimidinyl($C_{1-4}$)alkyl), alkenyl (especially $C_{3-4}$ alkenyl), aralkenyl (especially aryl($C_{3-4}$)alkenyl, such as phenyl($C_{3-4}$)alkenyl), alkynyl (especially $C_{3-4}$ alkynyl), alkoxycarbonyl (especially $C_{1-4}$ alkoxycarbonyl), alkanesulfonyl (especially $C_{1-4}$ alkylsulfonyl), arenesulfonyl (especially phenylsulfonyl), alkenyloxycarbonyl (especially $C_{3-4}$ alkenyloxycarbonyl), aralkyloxycarbonyl (especially phenyl ($C_{1-4}$)alkoxycarbonyl), aryloxycarbonyl (especially phenoxycarbonyl), heterocyclylalkyl (especially heterocyclyl($C_{1-4}$)alkyl, such as piperidinyl($C_{1-4}$)alkyl), carbamyl ($H_2NC(O)$), dithiocarboxyl or $XR^3$ (where X represents oxygen or a group $NR^4$), provided that when $R^2$ is alkenyl, aralkenyl or alkynyl said group does not have an unsaturated carbon atom bonding directly to the ring nitrogen of formula (I); $R^3$ and $R^4$ are, independently, hydrogen, alkyl (especially $C_{1-4}$ alkyl), aryl (especially phenyl), heteroaryl (especially pyridinyl or pyrimidinyl), aralkyl (especially aryl($C_{1-4}$)alkyl, such as phenyl($C_{1-4}$)alkyl), heteroarylalkyl (especially heteroaryl($C_{1-4}$)alkyl, such as pyridinyl($C_{1-4}$)alkyl or pyrimidinyl($C_{1-4}$)alkyl), alkenyl (especially $C_{2-4}$ alkenyl), aralkenyl (especially aryl($C_{2-4}$) alkenyl, such as phenyl($C_{2-4}$)alkenyl), alkynyl (especially $C_{2-4}$ alkynyl), heterocyclylalkyl (especially heterocyclyl($C_{1-4}$)alkyl, such as piperidinyl($C_{1-4}$)alkyl), alkoxycarbonyl (especially $C_{1-4}$ alkoxycarbonyl) or carboxylic acyl (especially $C_{1-4}$ alkylcarbonyloxy); alkyl moieties of $R^2$, $R^3$ and $R^4$ comprise from 1 to 15 carbon atoms, and are optionally substituted with one or more substituents selected from halogen, cyano, carboxyl (HOC(O)), carboxylic acyl (especially $C_{>4}$ alkylcarbonyloxy), carbamyl ($H_2NC(O)$), alkoxycarbonyl (especially $C_{1-4}$ alkoxycarbonyl), alkoxy (especially $C_{1-4}$ alkoxy), alkylenedioxy (especially $C_{1-4}$ alkylenedioxy), hydroxy, nitro, amino, acylamino (especially $C_{1-4}$ alkylcarbonylamino), imidate ($C_{1-4}$ alkyl[C(O)NHC(O)]) and phosphonato (OP(OH)$_2$) groups; aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl moieties of $R^2$, $R^3$ and $R^4$ comprise from 1 to 15 carbon atoms, and are optionally substituted with one or more substituents selected from, halogen, cyano, carboxyl (HOC(O)), carboxylic acyl (especially $C_{1-4}$ alkylcarbonyloxy), carbamyl ($H_2NC(O)$), alkoxycarbonyl (especially $C_{1-4}$ alkoxycarbonyl), alkoxy (especially $C_{1-4}$ alkoxy), alkylenedioxy (especially $C_{1-4}$ alkylenedioxy), hydroxy, nitro, haloalkyl (especially $C_{1-4}$ haloalkyl), alkyl (especially $C_{1-4}$ alkyl), amino, acylamino (especially $C_{1-4}$ alkylcarbonylamino), imidate ($C_{1-4}$ alkyl[C(O)NHC(O)]) and phosphonato (OP(OH)$_2$) groups; or an acid addition salt, quaternary ammonium salt or N-oxide derived therefrom.

In another aspect the present invention provides a compound of formula (I), wherein $R^1$ represents an optionally substituted 5-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to six carbon atoms, and $R^2$ represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; and acid addition salts and quaternary ammonium salts and N-oxides derived therefrom.

In yet another aspect the present invention provides a compound of formula (I) wherein $R^2$ is hydrogen, $C_{2-4}$ alkyl (substituted, but not on the α-carbon, with halogen (especially fluorine)), $C_{1-4}$ alkyl (optionally substituted with cyano), $C_{3-4}$ alkenyl, $C_{3-4}$ haloalkenyl, $C_{3-4}$ alkynyl or phenyl($C_{1-4}$)alkyl (wherein the phenyl ring is optionally substituted with halogen, $C_{1-4}$ alkyl, $C_{1-4}$ haloalkyl, $C_{1-4}$ alkoxy, $C_{1-4}$ haloalkoxy or cyano), provided that when $R^2$ is an unsubstituted or substituted alkenyl, or alkynyl group said group does not have an unsaturated carbon atom bonding directly to the ring nitrogen of formula (I).

In a further aspect the present invention provides a compound of formula (I) wherein $R^1$ is pyrrole, pyrazole, imidazole, 1,2,4-triazole, furan, thiophene, oxazole, isoxazole, thiazole or isothiazole all optionally substituted with one or more of halogen, $C_{1-4}$ alkyl, $C_{1-4}$ alkoxy, $C_{1-4}$ haloalkyl, mono($C_{1-4}$)alkylamino or di($C_{1-4}$)alkylamino; $R^2$ represents hydrogen, $C_{2-4}$ alkyl (substituted, but not on the α-carbon, with halogen (especially fluorine)), $C_{1-4}$ alkyl (optionally substituted with cyano), $C_{3-4}$ alkenyl, $C_{3-4}$ haloalkenyl, $C_{3-4}$ alkynyl or phenyl($C_{1-4}$)alkyl (wherein the phenyl ring is optionally substituted with halogen, $C_{1-4}$ alkyl, $C_{1-4}$ haloalkyl, $C_{1-4}$ alkoxy, $C_{1-4}$ haloalkoxy or cyano), provided that when $R^2$ is an unsubstituted or substituted alkenyl, or alkynyl group said group does not have an unsaturated carbon atom bonding directly to the ring nitrogen of formula (I).

In a further aspect the present invention provides a compound of formula (I) wherein $R^2$ is $C_{1-4}$ alkyl (optionally substituted with cyano, $CO_2(C_{1-4}$ alkyl) or phenyl (itself optionally substituted with halogen, $C_{1-4}$ alkyl, C, alkoxy, $C_{1-4}$ haloalkyl or $C_{1-4}$ haloalkoxy)), $C_{2-4}$ haloalkyl (the α-carbon being unsubstituted), $C_{3-4}$ alkenyl or $C_{3-4}$ alkynyl; provided that when $R^2$ is alkenyl or alkynyl said group does not have an unsaturated carbon atom bonding directly to the ring nitrogen of formula (I).

In a still further aspect the present invention provides a compound of formula (I) wherein $R^1$ is a pyrrole, thiophene or isoxazole ring optionally substituted with one or more of halogen, $C_{1-4}$ alkyl or $C_{1-4}$ haloalkyl; and $R^2$ is hydrogen, $C_{1-4}$ alkyl, $C_{2-4}$ fluoroalkyl (the α-carbon being unsubstituted, such as $FH_2CH_2C$, $F_2HCH_2C$ or $F_3CH_2C$), $C_{3-4}$ alkenyl (such as allyl) or $C_{3-4}$ alkynyl (such as propargyl), provided that when $R^2$ is an unsubstituted or substituted alkenyl, or alkynyl group said group does not have an unsaturated carbon atom bonding directly to the ring nitrogen of formula (I).

Specific compounds of formula (I) according to the invention include those set out in Table I below in which the groups represented by $R^1$ and $R^2$ are given for each compound, together with the melting point (° C.) or an indication of the physical state of the compound.

TABLE I

| Compound No | R¹ | R² | Melting Point |
|---|---|---|---|
| 1 | thiophen-3-yl | methyl | oil |
| 2 | thiophen-2-yl | methyl | oil |
| 3 | 2-methylpyrrol-3-yl | methyl | |
| 4 | 5-methylpyrrol-2-yl | methyl | |
| 5 | 5-chlorothiophen-3-yl | methyl | |
| 6 | thiazol-2-yl | 2,2-difluoroethyl | |
| 7 | 5-chlorothiazol-2-yl | 2,2,2-trifluoroethyl | |
| 8 | 5-trifluoromethylpyrazol-3-yl | methyl | |
| 9 | 2-methyloxazol-4-yl | allyl | |
| 10 | 3-methylisoxazol-5-yl | benzyl | |
| 11 | 1-methylimidazol-4-yl | 3-chlorobenzyl | |
| 12 | 1-methyl-1,2,4-triazol-3-yl | methyl | |
| 13 | 2-chloro-1,3,4-thiadiazol-5-yl | propargyl | |
| 14 | thiazolin-2-yl | methyl | |
| 15 | 5-chlorothiazol-2-yl | H | |
| 16 | 5-chlorothiazol-2-yl | 2,4-dichlorobenzyl | |
| 17 | 2-methylthiazol-4-yl | propyl | |
| 18 | 3-methylisothiazol-5-yl | 4,4-difluorobut-3-enyl | |
| 19 | 5-chlorothiophen-2-yl | H | |
| 20 | 5-bromothiophen-3-yl | methyl | |
| 21 | 4,5-dichlorofur-2-yl | 2-fluoroethyl | |
| 22 | 4-ethoxyfur-2-yl | methyl | |
| 23 | 2-dimethylaminothiazol-4-yl | allyl | |
| 24 | 3-trifluoromethyl-isoxazol-3-yl | methyl | |
| 25 | 5-methylthiophen-2-yl | 2,2-difluoroethyl | |
| 26 | 3-methoxy-1,2,4-triazol-5-yl | 4-fluorobenzyl | |
| 27 | 3-trifluoromethylpyrazol-4-yl | methyl | |
| 28 | isothiazol-4-yl | 2,2,2-trifluoroethyl | |
| 29 | 5-chlorothiazol-2-yl | 2,2-difluoroethyl | |
| 30 | 2,5-dichlorothiophen-2-yl | methyl | |
| 31 | 5-bromothiazol-2-yl | methyl | |
| 32 | 5-bromothiazol-2-yl | H | |
| 33 | 4,5-dichlorothiazol-2-yl | methyl | |
| 34 | 5-methoxythiazol-2-yl | methyl | |
| 35 | 2-methylthiazol-4-yl | 2-cyanoethyl | |
| 36 | 2-methylaminothiazol-4-yl | methyl | |
| 37 | 1-methylpyrrol-4-yl | methyl | |
| 38 | 3-methylisothiazol-5-yl | methyl | |
| 39 | 3-chloropyrrol-4-yl | methyl | |
| 40 | 1,3-dithiacyclopent-4-en-4-yl | methyl | |
| 41 | 3-methylisoxazol-5-yl | methyl | oil |
| 42 | 1-methylpyrrol-2-yl | benzyl | oil |
| 43 | benzoxazol-2-yl | methyl | oil |
| 44 | 2-chlorothiazol-5-yl | methyl | |
| 45 | 2-chlorothiazol-5-yl | 2,2,2-trifluoroethyl | |
| 46 | 2-chlorothiazol-5-yl | 2,2-difluoroethyl | |
| 47 | 2-chlorothiazol-5-yl | propargyl | |
| 48 | 2-chlorothiazol-5-yl | allyl | |
| 49 | 2-chlorothiazol-5-yl | H | |
| 50 | 3-chloroisothiazol-5-yl | methyl | |
| 51 | 3-chloroisothiazol-5-yl | 2,2,2-trifluoroethyl | |
| 52 | 3-chloroisothiazol-5-yl | 2,2-difluoroethyl | |
| 53 | 3-chloroisothiazol-5-yl | propargyl | |
| 54 | 3-chloroisothiazol-5-yl | allyl | |
| 55 | 3-chloroisothiazol-5-yl | H | |
| 56 | 3-methylisothiazol-5-yl | methyl | |
| 57 | 3-methylisothiazol-5-yl | 2,2,2-trifluoroethyl | |
| 58 | 3-methylisothiazol-5-yl | 2,2-difluoroethyl | |
| 59 | 3-methylisothiazol-5-yl | propargyl | |
| 60 | 3-methylisothiazol-5-yl | allyl | |
| 61 | 3-methylisothiazol-5-yl | H | |
| 62 | 2-methylthiazol-5-yl | methyl | |
| 63 | 2-methylthiazol-5-yl | 2,2,2-trifluoroethyl | |
| 64 | 2-methylthiazol-5-yl | 2,2-difluoroethyl | |
| 65 | 2-methylthiazol-5-yl | propargyl | |
| 66 | 2-methylthiazol-5-yl | allyl | |
| 67 | 2-methylthiazol-5-yl | H | |

The preparation of the compounds of formula (I) may be accomplished by use of one or more of the synthetic techniques described below and further illustrated in the Examples.

The compounds of formula (I) can be prepared from compounds of formula (II) by treating them with a suitable base, such as potassium carbonate, in the presence of compound of formula $R^2L$ where L is a suitable leaving group such as a halide, triflate or mesylate.

Alternatively, compounds of formula (I) can be prepared from compounds of formula (II) by reductive amination with an aldehyde ($R^5CHO$; wherein $R^5CH_2=R^2$) in the presence of a suitable reducing agent such as formic acid.

Compounds of formula (II) can be prepared by demethylating a compound of formula (III) by, for example, treating them with a chloroformate ester (such as vinyl chloroformate) to produce a carbamate, and subjecting the product so formed to acid hydrolysis.

Compounds of formula (III) can be prepared by treating 3-cyano-8-methyl-8-azabicyclo[3.2.1]octane (IV) with a suitable base, such as lithium diisoropylamide (LDA), and reacting the product so formed with a halide $R^1Hal$, wherein Hal is a halogen atom.

3-Cyano-8-methyl-8-azabicyclo[3.2.1]octane (IV) can be prepared by treating tropinone (V) with tosylmethyl isocyanide in the presence of a suitable base, such as potassium ethoxide. Alternatively, 3-cyano-8-methyl-8-azabicyclo[3.2.1]octane (IV) can be prepared by treating tropine (XIII) with thionyl chloride to give 3-chloro-8-methyl-8-azabicyclo[3.2.1]octane (XII) and reacting (XII) with cyanide as described in J. Am. Chem. Soc., (1958) 80, 4677.

Compounds of formula (I) can also be prepared by treating compounds of formula (VI) with a suitable base, such as lithium diisoropylamide (LDA), and reacting the product so formed with a halide $R^1Hal$, wherein Hal is a halogen atom.

Compounds of formula (VI) can be prepared by treating 3-cyano-8-azabicyclo[3.2.1]octane (VII) with a suitable base, such as potassium carbonate, in the presence of a halide $R^2L'$, wherein L' is a leaving group (especially halogen).

3-Cyano-8-azabicyclo[3.2.1]octane (VII) can be prepared by demethylating 3-cyano-8-methyl-8-azabicyclo[3.2.1]octane (IV) by, for example, treating them with a chloroformate ester (such as vinyl chloroformate) to produce a carbamate, and subjecting the product so formed to acid hydrolysis.

As a further alternative, compounds of formula (VI) can be prepared by treating compounds of formula (VIII) with tosylmethyl isocyanide in the presence of a suitable base, such as potassium ethoxide.

Compounds of formula (VIII) can be prepared by the Robinson tropinone synthesis, see, for instance, J. Chem. Soc., (1917) 111, 762. Alternatively, compounds of formula (VIII) can be prepared by reacting cyclohepta-2,6-dienone (XI) with an amine, $R^2NH_2$, as described in, for example, Tetrahedron, (1973) 155, Bull. Chem. Chem. Soc. Jpn., (1971) 44, 1708 or J. Org. Chem., (1971) 36, 1718.

Alternatively, compounds of formula (I) can be prepared by treating a compound of formula (IX) with an acetonitrile of formula (X) in the presence of a suitable base, for example sodium hydride. A similar process is described in J. Med. Chem., (1975) 18, 496.

In further aspects the present invention provides processes for preparing compounds of formula (I), as hereinbefore described, and the intermediates of formula (II) and (III).

In a further aspect the invention provides a method of combating insect and like pests at a locus by applying to the locus or the pests an insecticidally effective amount of an insecticidal composition comprising a compound of formula (I) or an acid addition salt, quaternary ammonium salt or N-oxide derived therefrom.

The compounds of formula (I) can be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of formula (I) include: *Myzus persicae* (aphid), *Aphis gossypii* (aphid), *Aphis fabae* (aphid), *Aedes aegypti* (mosquito), *Anopheles spp.* (mosquitos), *Culex spp.* (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), *Aonidiella spp.* (scale insects), *Trialeurodes spp.* (white flies), *Bemisia tabaci* (white fly), *Blattella germanica* (cockroach), *Periplaneta americana* (cockroach), *Blatta orientalis* (cockroach) *Spodoptera littoralis* (cotton leafworn), *Heliothis virescens* (tobacco budworm) *Chortiocetes terminifera* (locust), *Diabrotica spp.* (rootworms), *Agrotis spp.* (cutworms), *Chilo partellus* (maize stem borer), *Nilaparvata lugens* (planthopper), *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite), *Phyllcoptruta oleivora* (citrus rust mite), *Polyphagotarsonemus latus* (broad mite) and *Brevipalpus spp.* (mites). Further examples include insects which adversely affect the health of the public or of animals.

In order to apply the compounds of formula (I) to the locus of the nematode, insect or acarid pest, or to a plant susceptible to attack by the nematode, insect or acarid pest, the compound is usually formulated into a composition which includes in addition to a compound of formula (I) a suitable inert diluent or carrier material, and, optionally, a surface active agent. The amount of composition generally applied for the control of nematode pests gives a rate of active ingredient from 0.01 to 10 kg per hectare, preferably from 0.1 to 6 kg per hectare.

Thus in another aspect the present invention provides a insecticidal, acaricidal or nematicidal composition comprising an insecticidally, acaricidally or nematicidally effective amount of a compound of formula (I) and a suitable carrier or diluent therefor.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, Fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils, with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. In use, the concentrates are diluted in water and applied by means of a spray to the area to be treated.

Suitable liquid solvents for ECs include methyl ketones, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropyl-naphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or microcapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of formula (I) may be the sole active ingredient of the composition or it may be admixed with one or more additional active ingredients such as insecticides, synergists, herbicides, fungicides or plant growth regulators where appropriate. Suitable additional active ingredients for inclusion in admixture with a compound of formula (I) may be compounds which will broaden the spectrum of activity of the compositions of the invention or increase their persistence in the location of the pest. They may synergise the activity of the compound of formula (I) or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lamda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorfluazuron;

e) Organic tin compounds such as cyhexatin, fenbutatin oxide, azocyclotin;

f) Macrolides such as avermectins or milbemycins, for example such as abamectin, ivermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents;

k) Imidacloprid;

l) spinosad.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicide which can be included is propanil, an example of a plant growth regulator for use in cotton is "Pix", and examples of fungicides for use in rice include blasticides such as blasticidin-S. The ratio of the compound of formula (I) to the other active ingredient in the composition will depend upon a number of factors including type of target, effect required from the mixture etc. However in general, the additional active ingredient of the composition will be applied at about the rate at which it is usually employed, or at a slightly lower rate if synergism occurs.

The invention is illustrated by the following Examples. Examples 1–5 illustrate the preparation of a range of compounds of formula (I). Examples 6–13 illustrate compositions suitable for the application of the compounds of formula (I) according to the invention. The following ingredients are referred to by their Registered Trade Marks and have the composition as shown below.

| Registered Trade Mark | Composition |
|---|---|
| Synperonic NP8 | |
| Synperonic NP13 | Nonylphenol-ethylene oxide condensate |
| Synperonic OP10 | |
| Aromasol H | Alkylbenzene solvent |
| Solvesso 200 | Inert organic diluent |
| Keltrol | Polysaccharide |

Selected NMR data are presented in the Examples. For NMR data, no attempt has been made to list every absorption. The following abbreviations are used throughout the Examples:

| ppm = | parts per million | m = | multiplet |
|---|---|---|---|
| s = | singlet | brs = | broad singlet |
| dd = | doublet of doublets | | |

EXAMPLE 1

This Example illustrates the preparation of 3-(thiophen-3-yl)-3-cyano-8-methyl-8-azabicyclo[3.2.1]octane (Compound No. 1 of Table I).

Sodium hydride (0.367 g of a 50% dispersion in oil) was added portionwise to a stirred mixture of meso-2,5-bis(chloromethyl)-1-benzylpyrrolidine [prepared by washing meso-2,5-bis(chloromethyl)-1-benzylpyrrolidine hydrochloride (1.0 g) in dichloromethane with 2M sodium hydroxide solution and brine, drying (MgSO$_4$) and evaporating under reduced pressure] and 3-(cyanomethyl)thiophene (0.46 ml) in N,N-dimethylformamide (15 ml) at 0° C. under nitrogen. After 4 hours the mixture was allowed to warm to room temperature and stand overnight. The mixture was then cooled to 0° C., water added dropwise and the resulting mixture extracted with ethyl acetate (×3). The combined extracts were washed with water (×4) and brine, dried (MgSO$_4$) and evaporated under reduced pressure. Chromatography [SiO$_2$, hexane:tert-butyl methyl ether (100:0) to (90:10)] gave 3-(thiophen-3-yl)-3-cyano-8-methyl-8-azabicyclo[3.2.1]octane (0.40 g).

$^1$H NMR (270 MHz) in CDCl$_3$: δ7.5–7.1 (8 H, both isomers, m), 3.54 and 3.57 (2 H, both isomers, 2×s), 3.31 (2 H, both isomers, m), 2.78 (2 H, one isomer, dd), 2.4–2.0 (4 H one isomer and 6 H other isomer, m) and 1.41 and 1.28 (2 H, both isomers, m)ppm.

EXAMPLE 2

This Example illustrates the preparation of 3-(thiophen-2-yl)-3-cyano-8-methyl-8-azabicyclo[3.2.1]octane (Compound No. 2 of Table I).

Sodium hydride (0.367 g of a 50% dispersion in oil) was added portionwise to a stirred mixture of meso-2,5-bis(chloromethyl)-1-benzylpyrrolidine [prepared by washing meso-2,5bis(chloromethyl)-1-benzylpyrrolidine hydrochloride (1.0 g) in dichloromethane with 2M sodium hydroxide solution and brine, drying (MgSO$_4$) and evaporating under reduced pressure] and 2-(cyanomethyl)thiophene (0.46 ml) in N N-dimethylformamide (15 ml) at 0° C. under nitrogen. After 4 hours the mixture was allowed to warm to room temperature and stand overnight. The mixture was then cooled to 0° C., water added dropwise and the resulting mixture extracted with ethyl acetate (×3). The combined extracts were washed with water (×4) and brine, dried (MgSO$_4$) and evaporated under reduced pressure. Chromatography [SiO$_2$, hexane:tert-butyl methyl ether (100:0) to (90:10)] gave 3-(thiophen-2-yl)-3-cyano-8-methyl-8-azabicyclo[3.2.]octane (0.425 g).

$^1$H NMR (270 MHz) in CDCl$_3$: δ7.5–7.2 (6 H one isomer and 7 H other isomer, m), 7.13 (1 H one isomer, m), 7.05–6.95 (1 H, both isomers, m), 3.59 and 3.54 (2 H, both isomers, 2×s), 3.31 (2 H, both isomers, m), 2.81 (2 H, one isomer, dd), 2.4–1.95 (6 H, both isomers) and 1.50 (2 H, one isomer, dd)ppm.

EXAMPLE 3

This Example illustrates the preparation of exo-3-(3-methylisoxazol-5-yl)-endo-3-cyano-8-methyl-8-azabicyclo[3.2.1]octane (Compound No. 41 of Table I).

Potassium tert-butoxide (22.4 g) was added portionwise to a stirred mixture of tropinone (11.58 g) and tosylmethyl isocyanide (21.2 g) in dimethoxyethane (240 ml) and ethanol (8 ml) at 0° C. under nitrogen at such a rate to maintain the temperature between 0° C. and 10° C. The mixture was then allowed to warm to room temperature and stirred for a further 4 hours. After standing at room temperature for 3 days the mixture was filtered and the solid residue washed with dimethoxyethane. The filtrate was evaporated under reduced pressure and chromatographed [SiO$_2$; dichloromethane:methanol (90:10)] to give exo-3-cyano-8-methyl-8-azabicyclo[3.2.1]octane (9.1 g).

exo-3-Cyano-8-methyl-8-azabicyclo[3.2.1 ]octane (0.50 g) in tetrahydrofuran (5 ml) was added dropwise to a stirred solution of lithium diisopropylamide [made by adding n-butyl lithium (8.33 ml of a 1.6M solution in hexane) to diisopropylamine (1.346 g) in tetrahydrofuran (20 ml) at −70° C. under nitrogen and then stirring at −40° C. for 30 minutes] at −70° C. over 5 minutes. After 1.5 hours 1,1-dichloroethene (1.29 g) in tetrahydrofuran (5 ml) was added slowly. After 15 minutes the mixture was allowed to warm to room temperature and then stirred for 5 hours. Water (1 ml) was then added followed by ethyl acetate (150 ml). The mixture was dried (MgSO$_4$), evaporated under reduced pressure and chromatographed [SiO$_2$; dichloromethane:methanol (90:10)] to give exo-3-(1-chlorovinyl)-endo-3-cyano-8-methyl-8-azabicyclo[3.2.1]octane (0.41 g).

Potassium tert-butoxide (0.95 g) was added to a stirred solution of exo-3-(1-chlorovinyl)-endo-3-cyano-8-methyl-8-azabicyclo[3.2. 1]octane (0.90 g) in tetrahydrofuran (20 ml) at room temperature. After 4 hours the mixture was evaporated under reduced pressure and the residue absorbed onto neutral alumina which was then washed with ethyl acetate to give exo-3-ethynyl-endo-3-cyano-8-methyl-8-azabicyclo[3.2.1]octane (0.50 g).

Nitroethane (0.203 g) and triethylamine (0.045 g) in toluene (5 ml) were slowly added to a solution of exo-3-ethynyl-endo-3-cyano-8-methyl-8-azabicyclo[3.2.1]octane (0.40 g) and phenyl isocyanate (0.61 g) in toluene (10 ml) at room temperature. The mixture was heated to 100° C. for 2 hours and then allowed to cool to room temperature and filtered. The filtrate was evaporated under reduced pressure and chromatographed [SiO$_2$; dichloromethane: methanol (92.5:7.5)] to give exo-3-(3-methylisoxazol-5-yl)-endo-3-cyano-8-methyl-8-azabicyclo[3.2.1]octane (0.125 g).

$^1$H NMR (270 MHz) in CDCl$_3$: δ6.12 (1 H, s), 3.30 (2 H, m), 2.34 (3 H, s), 2.28 (3 H, s) and 2.45–2.10 (8 H, m)ppm.

EXAMPLE 4

This Example illustrates the preparation of 3-(1-methylpyrrol-2-yl)-3-cyano-8-benzyl-8-azabicyclo[3.2.1]octane (Compound No. 42 of Table I).

meso-2,5-bis(Chloromethyl)-1-benzylpyrrolidine hydrochloride (1.0 g) was dissolved in dichloromethane and the mixture washed with 2M sodium hydroxide solution. The aqueous layer was separated, extracted with dichloromethane and the combined organic phases were washed with brine, dried (MgSO$_4$) and evaporated under reduced pressure. The residue was dissolved in N-N-dimethylformamide (15 ml) and the solution cooled to 0° C. 2-Cyanomethyl-1-methylpyrrole (0.49 g) was added followed by portionwise addition of sodium hydride (0.734 g of a 50% dispersion in oil). After 5 hours at 0° C. the mixture was allowed to warm to room temperature and stand overnight. The mixture was then cooled to 0° C. and water cautiously added dropwise and the mixture extracted with ethyl acetate (×3). The combined extracts were washed with water (×4) and brine, dried (MgSO$_4$), evaporated under reduced pressure and chromatographed [SiO$_2$; hexane:tert-butyl methyl ether (100:0) to (80:20)] to give 3-(1-methylpyrrol-2-yl)-3-cyano-8-benzyl-8-azabicyclo[3.2.1]octane (0.098 g) as a 1:1 mixture of exo and endo isomers.

$^1$H NMR (270 MHz) in CDCl$_3$: δ7.51 (1 H, both isomers, m), 7.4–7.2 (4 H, both isomers, m), 6.59 (1 H, both isomers, m), 6.04 (2 H, both isomers, m), 3.89 and 3.88 (3 H, both isomers, 2×s), 3.54 (2 H, both isomers, brs), 3.33 (2 H, both isomers, m), 2.89 (2 H, one isomer, dd), 2.4–1.9 (6 H, both isomers, m) and 1.49 (2 H, one isomer, dd)ppm.

EXAMPLE 5

This Example illustrates the preparation of exo-3-(benzoxazol-2-yl)-endo-3-cyano-8-methyl-8-azabicyclo[3.2.1]octane (Compound No. 43 of Table I).

Lithium bis(trimethylsilyl)amide (6.5 ml of a 1M solution in tetrahydrofuran) was added dropwise to a stirred solution of exo-3-cyano-8-methyl-8-azabicyclo[3.2.1]octane (0.50 g) and 2-chlorobenzoxazole (0.516 g) in tetrahydrofuran (5 ml) at room temperature. After 3 hours water was added and the mixture extracted with ethyl acetate (×3). The combined extracts were washed with water and brine, dried (MgSO₄) and evaporated under reduced pressure to give exo-3-(benzoxazol-2-yl)-endo-3-cyano-8-methyl-8-azabicyclo[3.2.1]octane (0.78 g) m.p. 143–147° C.

$^1$H NMR (270 MHz) in CDCl$_3$: δ7.72 (1 H, m), 7.54 (1 H, m), 7.38 (2 H, m), 3.39 (2 H, m), 2.66 (2 H, dd), 2.38 (3 H, s) and 2.45–2.3 (6 H, m)ppm.

EXAMPLE 6

This Example illustrates an emulsifiable concentrate composition which is readily convertible by dilution with water into a liquid preparation suitable for spraying purposes.

The concentrate has the following composition:

|  | % Weight |
| --- | --- |
| Compound No. 1 | 25.5 |
| SYNPERONIC NP13 | 2.5 |
| Calcium dodecylbenzenenesulphonate | 2.5 |
| AROMASOL H | 70 |

EXAMPLE 7

This Example illustrates a wettable powder composition which is readily convertible by dilution with water into a liquid preparation suitable for spraying purposes. The wettable powder has the following composition:

|  | % Weight |
| --- | --- |
| Compound No. 13 | 25.0 |
| Silica | 25.0 |
| Sodium lignosulphonate | 5.0 |
| Sodium lauryl sulphate | 2.0 |
| Kaolinite | 43.0 |

EXAMPLE 8

This Example illustrates a dusting powder which may be applied directly to plants or other surfaces and comprises 1% by weight of Compound No. 25 and 99% by weight of talc.

EXAMPLE 9

This Example illustrates a concentrated liquid formulation suitable for application by ultra low volume techniques after mixing with paraffinic diluents.

|  | % Weight |
| --- | --- |
| Compound No. 29 | 90.0 |
| SOLVESSO 200 | 10.0 |

EXAMPLE 10

This Example illustrates a capsule suspension concentrate which is readily convertible by dilution with water to form a preparation suitable for application as an aqueous spray.

|  | % Weight |
| --- | --- |
| Compound No. 43 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 76.4 |

EXAMPLE 11

A ready for use granular formulation:

|  | % Weight |
| --- | --- |
| Compound No. 4 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 12

An aqueous suspension concentrate:

|  | % Weight |
| --- | --- |
| Compound No. 8 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 13

This Example illustrates a water dispersible granule formulation.

|  | % Weight |
| --- | --- |
| Compound No. 20 | 5 |
| Silica | 5 |
| Sodium lignosulphate | 10 |
| Sodium dioctylsulphosuccinate | 5 |
| Sodium acetate | 10 |
| Montmorillonite powder | 65 |

EXAMPLE 14

This Example illustrates the insecticidal properties of the compounds of formula (I). The activity of the compounds of formula (1) was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYNPERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment.

The results of the tests against peach aphid (*Myzus persicae*) are presented below. The results indicate a grading of mortality (score) designated as A, B or C wherein C indicates less than 40% mortality, B indicates 40–79% mortality and A indicates 80–100% mortality; "–" indicates that either the compound was not tested or no meaningful result was obtained. In this test Chinese cabbage leaves were infested with aphids, the infested leaves were sprayed with the test composition, and the mortality assessed after 3 days. Compound No. 1 gave a grading of A.

Chemical Formulae Referred to in the Description

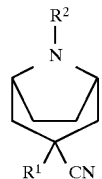
(I)

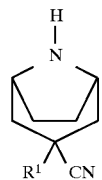
(II)

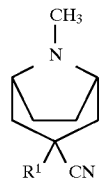
(III)

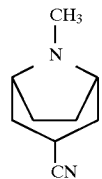
(IV)

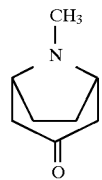
(V)

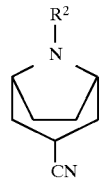
(VI)

-continued
Chemical Formulae Referred to in the Description

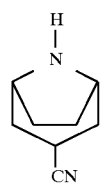
(VII)

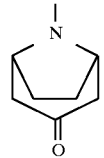
(VIII)

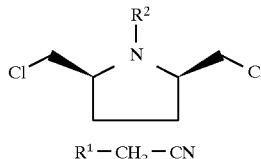
(IX)

$R^1-CH_2-CN$ (X)

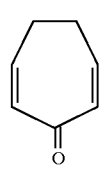
(XI)

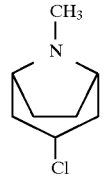
(XII)

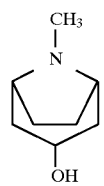
(XIII)

We claim:
1. A compound of formula (I):

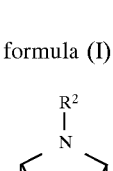
(I)

wherein $R^1$ is an optionally substituted 5-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to eight carbon atoms, and wherein two substituents may join to form a fused ring; $R^2$ represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or XR³ (where X represents oxygen or a group NR⁴), provided that when R² is alkenyl, aralkenyl or alkynyl said group does not have an unsaturated carbon atom bonding directly to the ring nitrogen of formula (I); R³ and R⁴ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of R², R³ and R⁴ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; or an acid addition salt, quaternary ammonium salt or N-oxide derived therefrom.

2. A compound according to claim 1 wherein R¹ represents an optionally substituted 5-membered ring system based on: pyrrole, pyrazole, imidazole, 1,2,3- or 1,2,4-triazole, furan, thiophene, oxazole, isoxazole, thiazole, isothiazole, 1,2,3- or 1,3,4-oxadiazole, or 1,2,3- or 1,3,4-thiadiazole, or a partially reduced form of one of the foregoing containing one double bond; or an oxathiole, dioxole or dithiole ring containing one double bond.

3. A compound of formula (I) as claimed in claim 1 wherein R² is hydrogen, $C_{2-4}$ alkyl (substituted, but not on the α-carbon, with halogen), $C_{1-4}$alkyl (optionally substituted with cyano), $C_{3-4}$alkenyl, $C_{3-4}$haloalkenyl, $C_{3-4}$alkynyl or phenyl($C_{1-4}$)alkyl (wherein the phenyl ring is optionally substituted with halogen, $C_{1-4}$alkyl, $C_{1-4}$haloalkyl, $C_{1-4}$alkoxy, $C_{1-4}$haloalkoxy or cyano), provided that when R² is an unsubstituted or substituted alkenyl, or alkynyl group said group does not have an unsaturated carbon atom bonding directly to the ring nitrogen of formula (I).

4. A compound of formula (I) as claimed in claim 1 wherein R¹ is pyrrole, pyrazole, imidazole, 1,2,4-triazole, furan, thiophene, oxazole, isoxazole, thiazole or isothiazole all optionally substituted with one or more of halogen, $C_{1-4}$alkyl, $C_{1-4}$alkoxy, $C_{1-4}$haloalkyl, mono($C_{1-4}$)alkylamino or di($C_{1-4}$)alkylamino.

5. A compound of formula (I) as claimed in claim 1 wherein R¹ is a pyrrole, thiophene or isoxazole ring optionally substituted with one or more of halogen, $C_{1-4}$ alkyl or $C_{1-4}$ haloalkyl; and R² is hydrogen, $C_{1-4}$ alkyl, $C_{2-4}$ fluoroalkyl (unsubsituted on the α-carbon), $C_{3-4}$ alkenyl or $C_{3-4}$ alkynyl), provided that when R² is an unsubstituted or substituted alkenyl, or alkynyl group said group does not have an unsaturated carbon atom bonding directly to the ring nitrogen of formula (I).

6. An intermediate compound of formula (II) or (III)

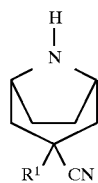
(II)

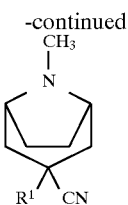
(III)

7. An insecticidal, acaricidal or nematicidal composition comprising an insecticidaly, acaricidally or nematicidally effective amount of a compound of formula (I) as claimed in claim 1 and a suitable carrier or diluent therefor.

8. A method of combating and controlling insect, acarine or nematode pests at a locus which comprises treating the pests or the locus of the pests with an effective amount of a compound as claimed in claim 1.

9. A method according to claim 8 wherein the pests are insect pests of growing plants.

10. A method of preparing a compound of formula (I) as claimed in claim 1 which comprises:

(a). reacting a compound of formula (IX):

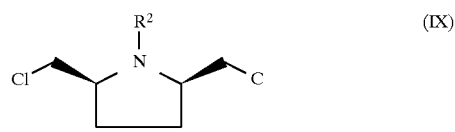
(IX)

with a compound of formula (X):

(X)

R¹—CH₂—CN in the presence of a base;

(b). reacting a compound of formula (VI):

(VI)

with a compound of formula R¹Hal, wherein Hal is a halogen, in the presence of a base; or, (c). reacting a compound of formula (II):

(II)

with a compound of formula R²L, wherein L is a suitable leaving group, in the presence of a base.

11. A method of combating and controlling insect, acarine or nematode pests at a locus which comprises treating the pests or the locus of the pests with an effective amount of a composition according to claim 7.

* * * * *